(12) United States Patent
Brock et al.

(10) Patent No.: US 7,357,922 B1
(45) Date of Patent: Apr. 15, 2008

(54) MICROEMULSION CONTAINING ALKANOLAMMONIUM SALTS OF FATTY ALCOHOL SULFATES AND/OR ALKYLPOLYALKYLENEGLYCOETHER-SULFATES

(75) Inventors: Michael Brock, Schermbeck (DE); Martin Stolz, Duelmen (DE); Sabine Diesveld-Koller, Gescher (DE); Eva-Maria Koberstein, Recklinghausen (DE); Ursula Michel, Dorsten (DE); Heinz Napierala, Herten (DE)

(73) Assignee: Sasol Germany GmbH, Hamburg (DE)

( * ) Notice: Subject to any disclaimer, the term of this patent is extended or adjusted under 35 U.S.C. 154(b) by 0 days.

(21) Appl. No.: 09/890,696

(22) PCT Filed: Feb. 7, 2000

(86) PCT No.: PCT/DE00/00357

§ 371 (c)(1),
(2), (4) Date: Dec. 16, 2001

(87) PCT Pub. No.: WO00/47166

PCT Pub. Date: Aug. 17, 2000

(30) Foreign Application Priority Data

Feb. 8, 1999 (DE) ................................ 199 04 847

(51) Int. Cl.
*A61K 8/00* (2006.01)
*A61K 8/02* (2006.01)
*A61K 9/00* (2006.01)

(52) U.S. Cl. .................... 424/70.24; 424/401; 424/70.1
(58) Field of Classification Search ................ 424/401, 424/70.24, 70.1
See application file for complete search history.

(56) References Cited

U.S. PATENT DOCUMENTS

| 4,371,548 | A |   | 2/1983  | Hermann et al. |
|-----------|---|---|---------|----------------|
| 4,797,272 | A |   | 1/1989  | Linn et al. |
| 5,077,040 | A | * | 12/1991 | Bergmann et al. ............ 424/70 |
| 5,605,651 | A | * | 2/1997  | Balzer ........................ 252/312 |
| 5,612,300 | A |   | 3/1997  | von Bluecher et al. |
| 5,653,988 | A |   | 8/1997  | Gerber et al. |
| 5,695,775 | A |   | 12/1997 | von Bluecher et al. |
| 6,132,738 | A |   | 10/2000 | Lerg et al. |
| 6,235,696 | B1 |  | 5/2001  | Hensen et al. |
| 6,235,913 | B1 |  | 5/2001  | Raths et al. |

FOREIGN PATENT DOCUMENTS

| DE | 3534733    |   | 4/1987 |
|----|------------|---|--------|
| DE | 19755488   |   | 9/1999 |
| EP | 0387647 A3 |   | 9/1990 |
| EP | 0638634 A2 |   | 2/1995 |
| EP | 0 771 559  | * | 5/1997 |
| WO | WO 95/12379 |  | 5/1995 |

OTHER PUBLICATIONS

V. Chhabra, M.L. Free, P.K. Kang, S.E. Truesdail, and D.O. Shah, "Microemulsions as an Emerging Technology," *Tenside Surf. Det.* 34 (1997) 3, pp. 156-168.

* cited by examiner

Primary Examiner—Shengjun Wang
(74) Attorney, Agent, or Firm—Browning Bushman P.C.

(57) ABSTRACT

This invention relates to microemulsions containing alkanolammonium salts of the alkylsulfates and/or alkylpolyalkyleneglycolethersulfates, water, one or more oil component(s), and one or more alcohol(s). The invention also relates to the use thereof for cosmetic and/or medicinal-dermatologic applications.

8 Claims, No Drawings

MICROEMULSION CONTAINING ALKANOLAMMONIUM SALTS OF FATTY ALCOHOL SULFATES AND/OR ALKYLPOLYALKYLENEGLYCOETHER-SULFATES

BACKGROUND OF THE INVENTION

1. Field of the Invention

The present invention relates to microemulsions containing alkanolammonium salts of the alkylsulfates and/or alkylpolyalkyleneglycolethersulfates and the use thereof for cosmetic and/or medicinal-dermatologic applications.

2. Description of the Prior Art

In particular, microemulsions are increasingly used for applications in which it is desirable to simultaneously employ an aqueous phase and an oil component. For a survey of microemulsion applications, see e.g. Chhabra, V., et al. in *Tensid Surf. Det.*, 34 (1997), p. 156-168. In said publication for example the use of microemulsions in cleansers is described.

There is also an interest in emulsions for cosmetic and medicinal-dermatologic applications. Compositions which are intended for use both as body cleaners and body care preparations must fulfill different requirements, e.g. combining the cleaning properties of an aqueous surfactant formulation with the cosmetic properties of an oil component. The compositions of preparations employed both as body cleaners and body care preparations are different from conventional cleaners utilized for instance for cleaning floors, textiles, or dishes.

Skin and hair are usually cleaned with surfactants, which will effect more or less pronounced swelling and subsequent dehydration of the horn layer of the skin, thereby impairing the protective mechanism of the skin surface. Therefore, skin care components allowing regeneration of the skin are increasingly added to customary skin cleaning preparations. It is furthermore possible to add excitometabolic components to these preparations, thus improving the general condition. This is particularly true of foam bath oils, which have been commercially available lately. Besides other active ingredients, these substantially anhydrous preparations contain surfactants for cleaning the skin and a large quantity of oils for treating the skin. The disadvantage of the foam bath oils is that the major portion of the oil remains on the water surface in the bath tub, thus having only little contact with the skin and a poor regenerating effect. The oil remains largely unused in the waste water.

The facts are similar with shower oil preparations, e.g. those described in U.S. Pat. No. 5,653,988 or DE 197 12 678-A1. The formulations disclosed therein are substantially anhydrous, surfactant-containing, cosmetic or dermatologic shower oils, which contain at least 45% or 30% of one or more oil component(s). With these products, too, the major portion of the oil components is washed away unused when taking a shower bath because the oil in the products is present in excess.

Another disadvantage of foam bath oils and shower oils is the high price of the ingredients, which contain no or only little water. Therefore, many efforts have hitherto been made to reduce the oil content, while increasing the water content, preserving the foaming power, and improving the price/performance ratio.

U.S. Pat. No. 4,371,548 discloses foaming and surfactant-containing bath and shower preparations having an oil content of from 20 to 60% and, optionally, a water content of max. 15%. These preparations have disadvantages and furthermore still have a poor price/performance ratio because the water content is kept low in order to preserve the desirable properties (good cleaning of the skin, good foaming power, intense skin care effect).

The type of oil component, the amount used in a formulation, the percentage of the aqueous phase and its composition are frequently predetermined by the requirements of the individual fields of application. While the expert knows how to select an appropriate surfactant from among the large variety of commercially available products for making a macroemulsion, the manufacture of a microemulsion presents considerable problems because the phase areas of an oil-water-surfactant blend, wherein a macroemulsion is formed, are considerably larger than those in which microemulsions are formed.

Numerous attempts were made in the past to manufacture preparations, which are both body cleaners and body care products. The terms "body cleaner" and "body care product" used herein shall mean any product employed for cleaning and treating hair and/or skin during showering, washing, or bathing.

When employing the compositions of the present invention for cosmetic and medicinal-dermatologic applications, it has been surprisingly discovered that the microemulsions of the invention are capable of combining the cleaning properties of an aqueous surfactant formulation and the cosmetic properties of an oil component, thereby effecting better spreading of the cosmetic oil component on the skin as a result of the fine dispersion of the oil droplets in the microemulsion.

When formulating cosmetic or medicinal-dermatologic preparations, the problem is aggravated by the fact that the surfactants employed for making the microemulsions should be non-irritant to the skin, the selection of a suitable surfactant thus being more difficult.

The microemulsions described in literature mostly comprise nonionic surfactants, e.g. alcohol ethoxylates. When using these surfactants in preparations intended for application to human skin, they have the disadvantage to cause intolerably high defatting of the skin. Anionic surfactants often require co-emulsifiers to make microemulsions.

Microemulsions containing alkylpolyalkyleneglycolethersulfates or alkylsulfates are known per se. DE 35 34 733 A1 discloses foaming surfactant preparations with clear-solubilized, water-insoluble oil components, which are usually termed microemulsions. In said publication it is explicitly pointed out that lower alcohols or alkylglycols having $C_1$- to $C_4$-alkyl groups need not be employed. EP 0 638 634 A2 discloses surfactant microemulsions as all-purpose cleaners, which inevitably contain surfactants of the sulfonate type. However, such surfactants are inappropriate for cosmetic applications.

SUMMARY OF THE INVENTION

It was the object of the present invention to solve the aforementioned problems observed when formulating cosmetic and medicinal-dermatologic microemulsions by providing surfactants for the preparation of microemulsions having an oil content of max. 20%, a high water content, and a surfactant content as low as possible.

It has surprisingly been found that cosmetic and medicinal-dermatologic preparations, especially bath and shower preparations, but also liquid soaps and shampoos presenting the required characteristics can be formulated as microemulsions having a lower oil content and a higher water content.

DESCRIPTION OF THE PREFERRED EMBODIMENTS

The subject matter of the invention relates to microemulsions containing
(A) 0.5 to 70% by weight of alkanolammonium salts of the alkylsulfates and/or alkylpolyalkyleneglycolethersulfates having the following structure

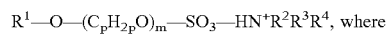

| | |
|---|---|
| $R^1 =$ | is a $C_8$- to $C_{20}$-hydrocarbon residue, |
| $p =$ | is an integer from 2 to 5, where p can be different for each m, |
| $R^2 =$ | H, a $C_1$- to $C_6$-alkyl, or a $C_2$- to $C_4$-hydroxyalkyl, |
| $R^3 =$ | H, a $C_1$- to $C_6$-alkyl, or a $C_2$- to $C_4$-hydroxyalkyl, |
| $R^4 =$ | a $C_2$- to $C_4$-hydroxyalkyl, preferably a $C_3$-hydroxypropyl, and |
| $m =$ | is an integer from 0 to 7, |

(B) 20 to 95% by weight of water,
(C) 0.1 to 20% by weight of one or more oil component(s), and
(D) 0.1 to 20% by weight, preferably 0.1 to 15% by weight of one or more mono- or polyhydric, preferably mono-, di-, or trihydric $C_2$- to $C_{24}$-alcohol(s), preferably $C_2$- to $C_6$-alcohol(s).

Moreover, the microemulsions of the subject invention can contain at least one of the following components:
(E) 0 to 20% by weight, preferably 3 to 15% by weight of one or more additional surfactant(s)
(F) 0 to 20% by weight, preferably 1 to 12% by weight, or 3 to 12% by weight of one or more electrolyte(s), and
(G) 0 to 10% by weight, preferably 0.1 to 8% by weight of one or more additive(s).

More advantageously, the microemulsions contain the abovementioned components independently of one another in the quantities set forth hereinbelow:
(A) 2 to 60% by weight, preferably 20 to 40% by weight,
(B) 30 to 80% by weight, preferably 40 to 60% by weight,
(C) 0.5 to 15% by weight, preferably 4 to 10% by weight,
(D) 0.1 to 9% by weight, preferably 0.5 to 9% by weight,
(E) 0 to 20% by weight, preferably 3 to 15% by weight of additional surfactants,
(F) 0 to 20% by weight, preferably 1 to 12% by weight of electrolytes, and
(G) 0 to 10% by weight, preferably 0.1 to 8% by weight of additives, wherein furthermore most advantageously:
(E) as an additional surfactant is a triglyceride alkoxylated with ethyleneoxide and/or propyleneoxide and subsequently esterified, wholly or in part, with $C_6$- to $C_{22}$-fatty acids, and/or
(G) as at least one additive is a poly($C_2$- to $C_4$-) alkyleneglycol having a molecular weight of up to 1,500 g/mole.

Contrary to emulsions, the microemulsions of the present invention are thermodynamically stable, optically transparent, macroscopically homogeneous mixtures of two liquids, which are incapable of being mixed with each other, namely, water (B) and an oil component (C) to which the surfactant molecules mentioned above under (A) were added. The microemulsions of the invention can be prepared, for example, at temperatures ranging from 20 to 80° C., preferably below 55° C. They are stable up to 60° C. The average particle size of the dispersed phase is preferably less than 100 nm.

The microemulsions as claimed herein normally do not form mesomorphous phases within a wide range of compositions. They are most suitable for cosmetic and/or medicinal-dermatologic applications. In particular, they are employed as or in body cleaners or body care preparations.

The microemulsions according to the present invention are low-priced preparations, which can be readily manufactured. They are distinguished by good foaming power and high detersive efficiency. Owing to the oil content, said microemulsions have a regenerating effect on the general condition of the skin, reduce the feeling of dryness of the skin, and make the skin supple.

The compositions according to the present invention most preferably contain alkanolammonium salts of the alkylsulfates and/or alkylpolyalkyleneglycolethersulfates of the aforesaid general structure. Preferably, they have independently of one another the following radicals:

| | |
|---|---|
| $R^1 =$ | $C_{12}$- to $C_{16}$-alkyl, the alkyl residue being linear and saturated, |
| $p =$ | 2 or 3, where p can be different for each m, |
| $R^2 =$ | H or hydroxyisopropyl, |
| $R^3 =$ | H or hydroxyisopropyl, |
| $R^4 =$ | hydroxyisopropyl, and |
| $m =$ | 0, 1, or 2. |

Advantageous embodiments of the present invention with respect to the components (C) to (G) are set forth hereinbelow.

Oil Component (C)

The oil components of the present invention are advantageously chosen from the group of lecithins and the group of mono-, di-, and/or triglycerides of saturated and/or unsaturated, branched and/or linear alkylcarboxylic acids having chain lengths of from 8 to 24, particularly from 12 to 18 carbon atoms. The fatty acid triglycerides can advantageously be synthetic, semisynthetic, or natural oils, such as soya oil, castor oil, olive oil, safflower oil, wheatgerm oil, grapeseed oil, sunflower oil, peanut oil, almond oil, palm oil, coconut oil, thistle oil, evening primrose oil, rape oil, etc.

The oil component can furthermore comprise vaseline, paraffin oil, and polyolefins. Moreover, the oil components according to the present invention can advantageously be selected from the group of esters of saturated and/or unsaturated, branched and/or linear alkylcarboxylic acids having chain lengths of from 3 to 30 carbon atoms and of saturated and/or unsaturated, branched and/or linear alcohols having chain lengths of from 3 to 30 carbon atoms. It is furthermore advantageous to select the oil components from the group of esters of aromatic carboxylic acids and saturated and/or unsaturated, branched and/or linear alcohols having chain lengths of from 3 to 30 carbon atoms, which ester oils can advantageously be chosen from the group of isopropyl myristate, isopropyl palmitate, isopropyl stearate, isopropyl oleate, n-butyl stearate, n-hexyl laurate, n-decyl oleate, isooctylstearate, isononylstearate, isononylisononanoate, 2-ethylhexylpalmitate, 2-ethylhexyllaurate, 2-hexyldecyl-stearate, 2-octyldodecylpalmitate, oleyl oleate, oleyl erucate, erucyl oleate, erucyl erucate, and synthetic, semisynthetic, and natural mixtures of such esters, e.g. jojoba oil.

Furthermore, the oil component can advantageously be selected from the group of branched and linear hydrocarbons and hydrocarbon waxes and silicone oils. Any mixtures of the aforesaid oil components are also advantageous within the meaning of the present invention.

Alcohols (D)

The microemulsions claimed herein contain mono- or polyhydric, preferably mono-, di-, or trihydric $C_2$- to $C_{24}$-alcohols, preferably saturated and/or branched and/or linear alcohols. Examples of such alcohols include ethanol, propanol, isopropyl alcohol, butanol, pentanol, hexanol, heptanol, octanol, 2-ethylhexanol, lauryl alcohol, myristol alcohol, palmityl alcohol, steryl alcohol, oleyl alcohol, elaidyl alcohol, guerbet alcohols, and alkylene glycols, such as ethylene glycol, propylene glycol, and glycerol. Propylene glycol is particularly preferred.

Other Surfactants (E)

In addition to the abovementioned alkanolammonium salts of the alkylsulfates and/or alkylpolyalkyleneglycolethersulfates, the microemulsions of the present invention can contain additional surfactants, which are advantageously chosen from the group of alcohol polyethyleneglycolethers, e.g. of the general formula R—O—$(C_2H_4O)_n$—H, where R is a branched or linear, saturated or unsaturated $C_8$- to $C_{20}$-alkyl residue and n is a number from 2 to 20; fatty acid ester polyethyleneglycolethers, e.g. of the general formula R—COO—$(C_2H_4O)_p$—H, where R is a branched or linear, saturated or unsaturated $C_7$- to $C_{19}$-alkyl residue and p is a number from 2 to 40, alkyl polyalkyleneglycolethercarboxylic acids, e.g. of the general formula R—O—$(C_2H_4O)_n$—$CH_2$—COOH or the alkanol ammonium salts or alkali metal salts thereof, where R is a branched or linear, saturated or unsaturated $C_8$- to $C_{20}$-alkyl residue and n is a number from 2 to 20, alkylamidoalkylbetains, e.g. of the general formula R—CONH$(CH_2)_u$N$^+$$(CH_3)_2$—$CH_2$—COO—, where R is a branched or linear, saturated or unsaturated $C_7$- to $C_{19}$-alkyl residue and u is a number from 1 to 10, products obtained from the alkoxylation of triglycerides, which are esterified, wholly or in part, with $C_6$- to $C_{22}$-fatty acids, wherein 2 to 40 moles of alkoxylating agent are employed per mole of triglyceride, e.g. addition products of castor oil and/or dehydrated castor oil with ethyleneoxide, which are partially esterified with oleic acid.

Preferably, the microemulsions of the invention contain no or at most only small quantities (less than 1.5% by weight) of polyhydroxyfatty acid amides (so-called glucamides). Moreover, it is preferable that the composition of the invention contains no or at most only small amounts (less than 0.5% by weight) of anionic surfactants of the sulfonate type.

Electrolytes (F)

The microemulsions of the present invention may contain electrolytes. Examples thereof include alkali salts and alkaline earth salts, such as the corresponding halides, sulfates, phosphates, or citrates.

Additives (G)

Examples of additives include poly($C_2$- to $C_4$-)alkyleneglycols, particularly polyethylene glycols and/or polypropylene glycols, each preferably with a molecular weight of up to 1,500 g/mole, fragrances, colorants, hydrotropes, thickeners, pearlescent agents, protein hydrolysates, plant extracts, vitamins, antimicrobials and the like.

The following examples are merely illustrative and are not intended to constitute a limitation on the present invention. The term 'percent' shall mean 'percent by weight', based on the total weight of the respective microemulsion.

EXAMPLE 1

| | |
|---|---|
| MARLINAT ® 242/90 M | 25% |
| MARLIPAL ® 24/99 | 9% |
| Paraffin oil | 5% |
| NaCl | 8% |
| Fragrance, antioxidant, preservative | q.s. |
| Water | balance to 100% |

Preparation mix the first three components at 80° C. to obtain a homogeneous blend. Add aqueous NaCl at the same temperature. Then add fragrance, antioxidant, and preservative at 30° C.

EXAMPLE 2

| | |
|---|---|
| MARLINAT ® 242/90 M | 30% |
| n-Hexanol | 4% |
| Paraffin oil | 5% |
| NaCl | 4% |
| Fragrance, antioxidant, preservative | q.s. |
| Water | balance to 100% |

Preparation: As described in Example 1.

EXAMPLE 3

| | |
|---|---|
| MARLINAT ® 242/90 M | 38% |
| Paraffin oil | 5% |
| NaCl | 5% |
| Fragrance, antioxidant, preservative | q.s. |
| Water | balance to 100% |

Preparation

Mix the first two components at 80° C. to obtain a homogeneous blend. Add aqueous NaCl at the same temperature. Then add fragrance, antioxidant, and preservative at 30° C.

EXAMPLE 4

| | |
|---|---|
| MARLINAT ® 242/90 M | 28% |
| MARLIPAL ® 24/99 | 9% |
| Paraffin oil | 5% |
| Ampholyt JB 130 K | 9% |
| NaCl | 8% |
| Fragrance, antioxidant, preservative | q.s. |
| Water | balance to 100% |

Preparation

Mix the first three components at 80° C. to obtain a homogeneous blend. Add aqueous NaCl and component 4 at the same temperature. Then add fragrance, antioxidant, and preservative at 30° C.

EXAMPLE 5

| | |
|---|---|
| MARLINAT ® 242/90 M | 28% |
| MARLIPAL ® 24/99 | 9% |
| MARLINAT ® CM 105/80 | 5% |
| Paraffin oil | 5% |
| NaCl | 8% |
| Fragrance, antioxidant, preservative | q.s. |
| Water | balance to 100% |

Preparation

Mix the first four components at 80° C. to obtain a homogeneous blend. Add aqueous NaCl at the same temperature. Then add fragrance, antioxidant, and preservative at 30° C.

EXAMPLE 6

| MARLINAT ® 242/90 M | 30% |
| --- | --- |
| MARLIPAL ® 24/70 | 15% |
| Soybean oil | 5% |
| NaCl | 4% |
| Fragrance, antioxidant, preservative | q.s. |
| Water | balance to 100% |

Preparation: As described in Example 1.

EXAMPLE 7

| MARLINAT ® 242/90 M | 30% |
| --- | --- |
| MARLIPAL ® 24/70 | 10% |
| Paraffin oil | 5% |
| Na citrate | 4% |
| Fragrance, antioxidant, preservative | q.s. |
| Water | balance to 100% |

Preparation: As described in Example 1 except that aqueous Na citrate solution is used instead of aqueous NaCl solution.

EXAMPLE 8

| MARLINAT ® 242/90 T | 30% |
| --- | --- |
| MARLIPAL ® 24/60 | 10% |
| Paraffin oil | 5% |
| NaCl | 7% |
| Fragrance, antioxidant, preservative | q.s. |
| Water | balance to 100% |

Preparation

Mix the first three components at 50° C. to obtain a homogeneous blend. Add aqueous NaCl solution at the same temperature. Then add fragrance, antioxidant, and preservative at 30° C.

EXAMPLE 9

| MARLINAT ® 242/90 M | 28% |
| --- | --- |
| LIPOXOL ® 600 | 2% |
| MARLOWET ® LVS | 7% |
| Soybean oil | 4% |
| Castor oil | 1% |
| MARLINAT ® CM 105/80 | 4% |
| Ampholyt JB 130 K | 5% |
| NaCl | 2% |
| Fragrance, protein hydrolysate, thickener, antioxidant, preservative | q.s. |
| Water | balance to 100% |

Preparation

Mix the first six components at 20° C. to obtain a homogeneous blend. Add the remaining components at the same temperature.

EXAMPLE 10

| MARLINAT ® 242/90 M | 30% |
| --- | --- |
| LIPOXOL ® 600 | 2% |
| MARLOWET ® LVS | 5% |
| Soybean oil | 2% |
| Paraffin oil | 3% |

EXAMPLE 10-continued

| MARLINAT ® CM 105/80 | 4% |
| --- | --- |
| Ampholyt JB 130 K | 5% |
| NaCl | 2% |
| Fragrance, protein hydrolysate, thickener, antioxidant, preservative | q.s. |
| Water | balance to 100% |

Preparation: As described in Example 9.

The following products of CONDEA Chemie GmbH were used in Examples 1 to 10:

| MARLINAT ® 242/90 M | 90% of $C_{12}$- to $C_{14}$-alkylpolyethyleneglycol(2 EO)ether-sulfate-monoisopropanolammonium (MIPA) salt in 1,2-propyleneglycol |
| --- | --- |
| MARLINAT ® 242/90 T | 90% of $C_{12}$- to $C_{14}$-alkylpolyethyleneglycol(2 EO)ether-sulfate-triisopropanolammonium (TIPA) salt in 1,2-propyleneglycol |
| MARLIPAL ® 24/60 | $C_{12}$- to $C_{14}$-fatty alcohol polyethyleneglycol(6 EO)ether |
| MARLIPAL ® 24/70 | $C_{12}$- to $C_{14}$-fatty alcohol polyethyleneglycol(7 EO)ether |
| MARLIPAL ® 24/99 | 90% of $C_{12}$- to $C_{14}$-fatty alcohol polyethyleneglycol(9 EO)ether in water |
| MARLINAT ® CM 105/80 | 80% of $C_{12}$- to $C_{14}$-alkylpolyethyleneglycol(10 EO)ether carboxylic acid sodium salt in water |
| MARLOWET ® LVS | Ethoxylated castor oil, partially esterified with oleic acid |
| LIPOXOL ® 600 | Polyethyleneglycol 600 |
| Ampholyt JB 130 K | 30% of cocoamidopropyldimethylbetaine in water |

The formulations given herein as examples are outstanding in their high cleaning and foaming power, good initial foaming power, storage stability, and mildness to the skin.

The invention claimed is:

1. A microemulsion comprising:
   (A) 0.5 to 70% by weight of the alkanolammonium salts of alkylsulfates and alkylpolyalkyleneglycolethersulfates having the structure:

wherein
   $R^1$ is a $C_8$- to $C_{20}$-hydrocarbon residue,
   p is an integer from 2 to 5, wherein p can be different for each m,
   $R^2$ is H, a $C_1$- to $C_6$-alkyl, or a $C_2$- to $C_4$-hydroxyalkyl,
   $R^3$ is H, a $C_1$- to $C_6$-alkyl, or a $C_2$- to $C_4$-hydroxyalkyl,
   $R^4$ is a hydroxyisopropyl, and
   m is an integer from 0 to 7,
   and mixtures thereof;
   (B) 20 to 95% by weight water;
   (C) 0.1 to 20% by weight of at least one oil component; and
   (D) 0.1 to 20% by weight of at least one mono- or polyvalent $C_2$- to $C_{24}$-alcohol,
   each based on the total composition of the microemulsion, said microemulsion being optically transparent.

2. The microemulsion according to claim 1, wherein the alkanolammonium salts of the alkylsulfates and/or alkylpolyalkyleneglycolethersulfates comprise the following residue or indices:

$R^1$ is a linear and saturated $C_{12}$- to $C_{16}$-alkyl residue,
p is 2 or 3, wherein p can be different for each m,
$R^2$ is H or hydroxyisopropyl,
$R^3$ is H or hydroxyisopropyl,
$R^4$ is hydroxyisopropyl, and
m is an integer from 0 to 2.

3. The microemulsion according to any one of claims 1 and 2, wherein the microemulsion contains component
  (A) in an amount of 2 to 60% by weight,
  (B) in an amount of 30 to 80% by weight,
  (C) in an amount of 0.5 to 15% by weight, and
  (D) in an amount of 0.1 to 9% by weight.

4. The microemulsion according to any one of claims 1 and 2, further containing at least one of the following components:
  (E) 0 to 20% by weight of at least one surfactant,
  (F) 0 to 20% by weight of at least one electrolyte, and
  (G) 0 to 10% by weight of at least one additive, wherein (F) and (G) are exclusive of any ionic surfactant.

5. The microemulsion according to claim 4, containing at least one of the following components:
  (E) at least one additional surfactant comprising a triglyceride alkoxylated with ethyleneoxide and/or propyleneoxide and at least partially esterified with a $C_6$- to $C_{22}$-fatty acid, and
  (G) at least one additive comprising a poly($C_2$- to $C_4$-)alkyleneglycol having a molecular weight of up to 1,500 g/mole.

6. The microemulsion according to any one of claims 1 and 2, wherein the oil component (C) contains one or more components selected from the group consisting of lecithins; mono-, di-, and/or triglycerides of saturated and/or unsaturated, branched and/or linear carboxylic acids having chain lengths of from 8 to 24 carbon atoms; branched and/or linear hydrocarbons; waxes; petroleum jelly; paraffin oils; polyolefins; silicone oils; esters of saturated, unsaturated, and/or aromatic, branched and/or linear carboxylic acids having chain lengths of from 3 to 30 carbon atoms; and saturated and/or unsaturated, branched and/or linear alcohols having chain lengths of from 3 to 30 carbon atoms.

7. The microemulsion according to any one of claims 1 and 2, characterized in that the microemulsion is a stable and transparent emulsion, the disperse phase thereof having an average particle size of less than 100 nm.

8. A microemulsion consisting essentially of:
  (A) 0.5 to 70% by weight alkanolammonium salts of the alkylsulfates and/or alkylpolyalkyleneglycolethersulfates having the structure:

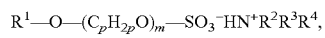

wherein
  $R^1$ is a $C_8$- to $C_{20}$-hydrocarbon residue,
  p is an integer from 2 to 5, wherein p can be different for each m,
  $R^2$ is H, a $C_1$- to $C_6$-alkyl, or hydroxyisopropyl,
  $R^3$ is H, a $C_1$- to $C_6$-alkyl, or $C_4$-hydroxyisopropyl,
  $R^4$ is a hydroxyisopropyl, and
  m is an integer from 0 to 7,
  and mixtures thereof;
  (B) 20 to 95% by weight water, and
  (C) 0.1 to 20% by weight one or more oil component(s), and
  (D) 0.1 to 20% by weight of one or more mono- or polyvalent $C_2$- to $C_{24}$-alcohol(s), and optionally
  (E) 0 to 20% by weight of one or more additional surfactant(s)
  (F) 0 to 20% by weight of one or more electrolyte(s), and
  (G) 0 to 10% by weight of one or more additive(s)
  each based on the total composition, and
  wherein no compound falls under two categories of (A) to (G) at the same time, said microemulsion being optically transparent.

* * * * *